United States Patent [19]

Keana

[11] Patent Number: 4,863,717
[45] Date of Patent: Sep. 5, 1989

[54] METHODS FOR CIRCUMVENTING THE PROBLEM OF FREE RADIAL REDUCTION ASSOCIATED WITH THE USE OF STABLE NITROXIDE FREE RADICALS AS CONTRAST AGENTS FOR MAGNETIC REASONANCE IMAGING

[75] Inventor: John F. W. Keana, Eugene, Oreg.

[73] Assignee: The State of Oregon Acting by and Through the State Board of Higher Education on Behalf of the University of Oregon, Eugene, Oreg.

[21] Appl. No.: 928,943

[22] Filed: Nov. 10, 1986

[51] Int. Cl.⁴ .................. A61K 49/00; A61B 5/05; A61B 6/00

[52] U.S. Cl. .................. 424/9; 128/653; 128/654; 436/173; 436/803; 436/806; 514/408; 514/645; 530/391; 548/542; 564/300; 424/417; 424/420; 424/450

[58] Field of Search ............ 424/9; 128/653, 654; 436/173, 803, 806; 564/300; 548/542; 514/645, 408; 530/391

[56] References Cited

U.S. PATENT DOCUMENTS 3,702,831 10/1970 Chiarelli et al.
3,704,235 11/1972 Rassat et al.
3,716,335  2/1973 Ullman et al.
4,099,918  7/1978 Keana.
4,622,294 11/1986 Kung et al. ............ 436/528
4,624,846 11/1986 Goldenberg ............ 530/388

FOREIGN PATENT DOCUMENTS 2137612 10/1984 United Kingdom.

OTHER PUBLICATIONS

Brasch et al., "Work in Progress: Nuclear Magnetic Resonance Study of a Paramagnetic Nitroxide Contrast Agent for Enhancement of Renal Structures in Experimental Animals", Radiology 147:773 (1983).
Cantenys et al., "Permeability of Liposomes Towards Amino Alcohol and Amino Acid Nitroxides", Chem. & Phys. of Lipids 33:303–312.
Couet et al., "Factors Affecting Nitroxide Reduction in Ascorbate Solution and Tissue Homogenates", Mag. Res. Imaging 3:83 (1985).
Curtet et al., "Selective Modification of NMR Relaxation Time in Human Colorectal Carcinoma by Using Gadolinium-Diethylenetriaminepentaacetic Acid Conjugated with Monoclonal Antibody 19-9", Proc. Natl. Acad. Sci. U.S.A., 83:4277–4281 (1986).
Ehman et al., "Enhanced MRI of Tumors Utilizing a New Nitroxyl Spin Label Contrast Agent", Mag. Res. Imiaging, 3:89–97 (1985).
Keana et al., "Influence of Structure on the Reduction of Nitroxide MRI Contrast-Enhancing Agents by Ascorbate", Physiol. Chem. & Phys. & Med. NMR, 16:477–480 (1984).
Keana et al., "Nitroxide-Doped Liposomes Containing Entrapped Oxidant: an Approach to the 'Reduction Problem' of Nitroxides as MRI Contrast Agents", Physiol. Chem. & Phys. & Med. NMR, 17:235–240 (1985).
Lovin et al., "Magnetic Field Dependence of Spin–Lattice Relaxation Enhancement Using Piperidinyl Nitroxyl Spin–Labels", Mag. Res. Imaging, 3:73 (1985).
Parasassi et al., "Paramagnetic Ions Trapped in Phospholipid Vesicles as Contrast Agents in NMR Imaging, 1, Mn-Citrate in Phosphatidylcholine and Phosphatidylserine Vesicles", Inorganica Chimica Acta, 106:135–139 (1985).

(List continued on next page.)

Primary Examiner—Robert J. Warden
Assistant Examiner—Stephen C. Wieder
Attorney, Agent, or Firm—Klarquist, Sparkman, Campbell, Leigh & Whinston

[57] ABSTRACT

Nitroxide contrast agents for MRI have a long useful life and can be administered in low concentration doses. Such agents include nitroxide-doped liposomes that encapsulate an oxidant and large molecules having surfaces covered with persistent nitroxide free radicals.

44 Claims, 1 Drawing Sheet

OTHER PUBLICATIONS

Swartz et al., "Hypoxia–Sensitive NMR Contrast Agents", *Mag. Res. in Med.*, 3:169–174 (1986).

Swartz et al., "Feasilibty of Measuring Oxygen and Redox Metabolism in vivo by NMR: Effeect of Paramagnetic Materials and their Cellular Metabolism on Relaxation Times of Protons of Water and Lipids", Period. Biol., 87:175 (1985).

Unger et al., "Magnetic Resonance Imaging Using Gadolinium Labeled Monoclonal Antibody", *Investigative Radiology*, 20:693–700 (1985).

Wesbey et al., "Paramagnetic Pharmaceuticals for Magnetic Resonance Imaging", *Physiol. Chem. & Phys. & Med. NMR*, 16:145–149 (1984).

Caride et al., "Relaxation Enhancement Using Liposomes Carrying Paramagnetic Species", *Mag. Res. Imaging*, 2:107–112 (1984).

Couet et al., "Pharmacokinetics and Metabolic Fate of Two Nitroxides Potentially Useful as Contrast Agents for Magnetic Resonance Imaging", *Pharm. Res.*, pp. 203–209 (1984).

Griffeth et al., "Pharmacokinetics of Nitroxide NMR Contrast Agents", *Invest. Radiol.*, 19:553–562 (1984).

Hupfer et al., "Liposomes from Polymerizable Phospholipids", *Chem. & Phys. of Lipids*, 33:355–374 (1983).

Newkome et al., "Cascade Molecules: Synthesis and Characterization of a Benzene[9]$^3$–Arborol", *J. Am. Chem. Soc.*, 108:849–850 (1986).

METHODS FOR CIRCUMVENTING THE PROBLEM OF FREE RADIAL REDUCTION ASSOCIATED WITH THE USE OF STABLE NITROXIDE FREE RADICALS AS CONTRAST AGENTS FOR MAGNETIC REASONANCE IMAGING

BACKGROUND OF THE INVENTION

This invention relates to spin-labelled contrast agents for magnetic resonance imaging. More specifically, it relates to such agents which can enhance contrast for a sustained period of time.

Magnetic resonance imaging (MRI) is a powerful noninvasive medical diagnostic technique that is currently in a period of rapid development. Agents which selectively enhance the contrast among various tissues, organs and fluids or of lesions within the body can add significantly to the versatility of MRI.

Liposomes, with compartments containing entrapped Mn-DTPA or some other paramagnetic substance, have been investigated as potential contrast agents for MRI, as described by Caride et al. in *Magn. Reson. Imaging* 2: 107–112 (1984). Liposomes tend to be taken up selectively by certain tissues such as the liver and are in general nonantigenic and stable in blood. They are used extensively as experimental drug delivery systems, as described by Poste et al. in "The Challenge of Liposome Targeting in Vivo", Chapter 1, *Lipsome Technology: Volume III, Targeted Drug Delivery and Biological Interaction*, G. Gregoriadis, Ed., CRC Press, Boca Raton, Fla. (1984). However, where tested for MRI in the past, liposomes have served merely as vessels to contain encapsulated paramagnetic material.

Owing to their paramagnetic nature and thus their ability to affect the relaxation times $T_1$ and $T_2$ of nearby nuclei, nitroxide free radicals constitute a class of potential MRI contrast-enhancing agents which are not toxic at low dosages. There are many examples of nitroxide-containing phospholipids, but these are invariably used in low concentrations merely to dope non-paramagnetic phospholipids for biophysical spin labeling studies, as described, for example, by Berliner, L. J., ed., in *Spin Labeling: Theory and Applications*, Academic Press, New York, volumes 1 and 2, 1976 and 1979 and by Holtzmann, J. L. in *Spin Labeling Pharmacology*, Academic Press, New York, 1984. European patent publication EP A 0160552, suggests that free radicals such as organic nitroxides may be enclosed within liposomes. The liposomes are said to be sufficiently leaky to water that, although the paramagnetic material is trapped inside, relaxation of bulk water can nevertheless occur by exchange of bulk water with inside water.

A more direct and reliable approach would be to incorporate nitroxide into the bilayer of the liposome. But, one would expect such a use of nitroxide to be hampered by a tendency of the paramagnetic nitroxyl group to accept an electron from the local environment and thus be reduced to a useless diamagnetic N-hydroxy compound, as described in Griffeth et al., *Invest. Radiol.* 19: 553–562 (1984); Couet, *Pharm. Res.* 5: 203–209 (1984); and Keana et al., *Physiol. Chem. Phys. and Med. NMR* 16: 477–480 (1984).

In the past, "reduction" problems have been handled by injecting large amounts of conventional nitroxide compounds into a subject with the intent of "swamping" the reduction reaction. Particularly large dosages have been required because there has been no practical way to direct nitroxide to specific tissues other than the liver and spleen. Because such nitroxides are rapidly diluted in body circulatory liquid, massive amounts of the contrast agent must be administered or the dilution effect renders the nitroxides ineffective as general contrast enhancers. The use of large dosages is not only wasteful and expensive, but also the large quantities of nitroxides and their metabolites can cause toxicity problems in sensitive subjects.

It would be helpful to target certain tissues, say cardiac tissue or tumor tissue, for contrast enhancement. If nitroxides could be concentrated in certain areas of the body, they would encounter fewer "reducing equivalents" than they would if carried throughout the entire body. To accomplish targeting, one thinks in terms of labeling an antibody or monoclonal antibody which seeks out the target tissue. But, it is clear that one or even a few nitroxides attached to an antibody will not provide enough enhancement. On the other hand, one cannot simply add hundreds directly to the antibody because that would almost surely destroy the antibody's ability to bind selectively to its target. Thus, a specific need has been to find a nontoxic contrast enhancing agent that can be targeted for specific tissues.

Prior patent publications such as EP A 0160552 and GB 2137612 describe the combined use of a contrast agent and a targeting agent such as an antibody. Such references do not, however, suggest how such targeting agents may be employed effectively with a nontoxic contrast agent such as a compound which effectively employs nitroxide free radicals.

SUMMARY OF THE INVENTION

Techniques have now been developed to provide long lasting nitroxide-bearing contrast agents without resorting to swamping of the reduction reaction or the use of leaky bilayers.

A first such technique is to provide a mechanism whereby the reduced form of a nitroxide group is continuously reoxidized back to the nitroxide. A lipsome is constructed to include a bilayer which incorporates long chain nitroxides so that the liposome itself can serve as a contrast enhancer. The nitroxide is not encapsulated so it can be reduced while exposed on the exterior surface of the liposome. An oxidant is entrapped in the internal aqueous compartment of the nitroxide-doped liposome, where it can regenerate a reduced nitroxide. Simple nitroxide fatty esters are known to undergo rapid ($t_{\frac{1}{2}} = <1$ sec) transbilayer motion ("flip-flop") as described by Birrell et al. in *Biochim. Biophys. Acta* 603: 213–219 (1980). Thus, reduced nitroxide groups eventually flip-flop to the inside of the liposome, are reoxidized to the nitroxide and flip-flop back to the exterior surface.

A second technique is to administer a relatively small number of large molecules, such as arborols, or assemblied of molecules such as liposomes, that have surfaces covered with numerous persistent nitroxide free radicals. The reduction problem is thus addressed through the sheer number of nitroxides on a given molecule.

With either technique, it is possible to target the nitroxide contrast agent by binding it to a targeting agent such as an antibody, carbohydrate, or other cell recognition targeting agent.

Accordingly, an object of this invention is to provide nitroxide-based contrast agents that have a long useful life after administration.

Another object is to provide nitroxide-based contrast agents which can be administered in low concentration doses.

A further object is to provide nitroxide agents which are specifically targeted for certain tissues.

These and other objects and advantages of the invention will be apparent from the following detailed description.

DETAILED DESCRIPTION

Contrast agents according to the present invention are substantially nontoxic molecules, particularly polymeric molecules, or assemblies of molecules which incorporate multiple reducible spin labels. For example, nitroxides of the type described in Keana, "Synthesis and Chemistry of Nitroxide Spin Labels," Chapter 1 in Holtzmann, J. L., ed., *Spin Labeling in Pharmacology*, Academic Press, New York (1984) and U.S. Pat. No. 4,099,918 can be located on the molecule or assembly of molecules in positions where they can contact surrounding bulk water and effect relaxation. As many as possible, but at least ten, nitroxide groups should be located on each molecule or assembly of molecules. Because the nitroxides are attached to a larger "particle", their rate of tumbling is slowed down to a more optimal value for effecting relaxation at the proton frequencies normally used in MRI applications. Rather than serving as a delivery system for some other contrast agent, nitroxide-bearing molecules and assemblies of molecules according to the present invention are themselves the structures that act as the contrast agents.

As used herein, "stable" describes any nitroxide group that can be isolated and characterized as such.

"Persistent" describes any nitroxide group that persists for hours in solution, but cannot necessarily be isolated.

"Liposome" refers to a particle which results from aggregation of amphiphilic molecules to form a bilayer structure, in a hollow, generally spherical form, with the polar sides facing both an internal water compartment and external bulk water.

Methods for forming liposomes are well known in the art. Typically, molecules form liposomes in aqueous solution when they contain at least two long hydrocarbon-like chains attached to a single polar group. Liposomes are commonly prepared from a phospholipid, for example, distearoyl phosphatidylcholine or lecithin. They may be formulated with cholesterol for added stability and may include other materials such as neutral lipids, and also surface modifiers such as positively or negatively charged compounds. A list of general liposome formulations can be found on page 6 of EP A 0160552. Depending on the techniques for their preparation, the envelope may be a simple bilayered spherical shell (a unilamellar liposome) or may have multiple layers within the envelope (multi-lamellar liposome).

The contrast agents of the present invention are administered in any common dosage form, typically in an injectable, physiologically compatible buffer liquid.

I. Entrapped Oxidant Liposome

Figure 1:
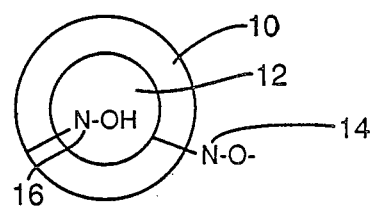
FIG. 1 is a schematic diagram of a liposome which includes an aqueous compartment containing an oxidant.

A first embodiment of the invention is a liposome which comprises a bilayer 10 shaped to define a compartment 12 as shown in FIG. 1. Incorporated into the bilayer 10 are multiple spin labels, particularly long chain nitroxides 14, which serve as water relaxation agents. Preferably, nitroxides have long hydrophobic tails so that they are held in the liposome and therefore the tumbling rate of the nitroxide group is slowed to a value more nearly that of the proton Larmor precessional frequency. This is important in order to achieve maximal contrast enhancement.

Because the nitroxides 14 are subject to reduction, and thus loss of contrast enhancement capability, the compartment 12 includes a supply of an oxidant which is capable of oxidizing a hydroxyl amine group to the corresponding nitroxide. The oxidant must be substantially incapable of passing through the bilayer 10. Most electrically charged oxidants cannot pass through due to their charges. Metal ions such as $Cu^{2+}$ with air or oxygen and persulfate ions, and organic peracids, are well suited oxidants.

Each nitroxide group 14 periodically flips into and out of the compartment 12. Should the nitroxide be reduced to an N-hydroxy group 16 while it is outside the compartment, it will be reoxidized at such time as it flips into the compartment and comes into contact with the oxidant substance.

The liposome may be prepared from virtually any type of molecules that form liposomes, the only requirement is that the nitroxide must be able to flip-flop and the liposome must remain impermeable to the entrapped oxidant for a sufficient period of time to complete the MRI procedure.

EXAMPLE 1

As an example, 1,4-Dihydroxy-2,2,6,6-tetramethylpiperidine (1)

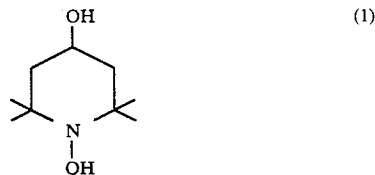

was prepared by Pt-catalyzed hydrogenation of 4-hydroxy-2,2,6,6,-tetramethylpiperidinoxyl (2) (Aldrich Chemical Co. of Milwaukee, Wis., U.S.A.) following the procedure of H. Schule, *Tetrahedron* 29: 4007-4011 (1973)

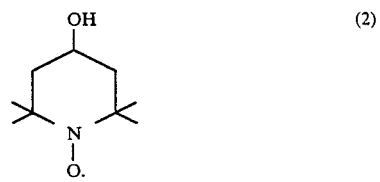

The piperidinoxyl (2) was acylated with palmitoyl chloride, by the procedure of E. G. Rozantsev, *Free Nitroxide Radicals*, H. Ultich Ed., Plenum Press, New York, p.

216 (1970), to prepare the nitroxide (3), which is now available commercially from Molecular Probes, Inc., of Junction City, Oreg., U.S.A.

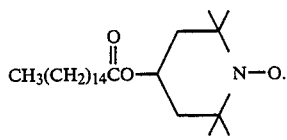

(3)

Egg yolk lecithin (EYL) as purchased from Sigma Chemical Co., of St. Lousi, Mo., U.S.A. as a $CHCL_3$ solution (100 mg/mL). X-Band ESR spectra were recorded on a Varian E-line spectrometer equipped with a temperature controller and interfaced with a Varian 620L-100 computer. UV-visible spectra were recorded on a Beckman DU-7 spectrometer equipped with a temperature controller.

Oxidation of (1) with $K_3Fe(CN)_6$

Deoxygenated ($N_2$ bubbling) 1.8–2.1 mMolar stock solutions at various pH values (4–8) of $K_3Fe(CN)_6$ and (1) were prepared separately of 0.05M TRIS HCl buffer, 0.1M KCl, and stored under $N_2$. A 1.0-mL aliquot of $K_3Fe(CN)_6$ stock solution was equilibrated (5° C., 15 min. $N_2$) in a quartz UV cuvette and then a 1.0-mL aliquot of chilled stock solution of (1) at the same pH was added with mixing. The rate of reduction of the $K_3Fe(CN)_6$ by (1) was monitored at 410 nm. At the end of a run (10–20 min) the colorless solution gave an ESR spectrum due to formation of nitroxide (2). This experiment demonstrates that $K_3Fe(CN)_6$ is capable of oxidizing an N-hydroxy molecule to the corresponding nitroxide group under physiologically compatible conditions.

Preparation of the Liposomes

The procedure of Tabushi et al., J. Am. Chem. Soc. 106: 219–226 (1984), was adapted. A $CHCl_3$ solution (100 μl) containing EYL (13 μMol) was added to a $CHCl_3$ solution (26 μl) containing nitroxide (3) (0.65 μMol, 10 mg/ml) and then the solvent was removed by a stream of $N_2$. The residue was dried in vacuo and the resulting film was suspended in 1.0 mL of a pH 8.0 aqueous solution which was 0.5M in $K_3Fe(CN)_6$, 0.5M in TRIS HCl buffer, and 0.1M in KCl. The mixture was sonicated under Ar with external ice cooling for 30 min. and then centrifuged at 5° C. for 30 min. at 12,000 rpm in order to remove any traces of titanium from the sonicator tip or any undispersed phospholipid. In order to separate the desired unilamellar liposomes from the larger multilamellar liposomes and free $K_3Fe(CN)_6$, the clear pale yellow supernatant was placed on a Sephadex 4B column (2 cm×17 cm) at 5° C. that was packed in and then eluted with 0.05M aqueous TRIS HCl buffer, pH 8.0, 0.1M KCl. The first two fractions (1–1.5 mL each) after the void volume consisted mainly of multilamellar liposomes (turbid yellow suspension). The next three clear yellow fractions containing the unilamellar liposomes (Lip-NO-Fe) were combined and stored under $N_2$ for the UV-visible reduction studies. Liposomes were used within 2–4 h of the gel filtration although results were essentially the same using liposomes that had been kept under $N_2$ at 5° C. for 12 h. Nitroxide-free liposomes (Lip-Fe) containing entrapped $K_3Fe(CN)_6$ were prepared in a similar manner.

The next six fractions were collected, combined and concentrated (stirred at 0° C., $N_2$) by ultrafiltration (Diaflow apparatus with membrane PM 10, cutoff 10,000 MW) to 1 mL. Then 6 mL of chilled 0.06M TRIS HCl buffer, pH 8, 0.1M KCl was added to the concentrated Lip-NO-Fe and then reconcentrated to 1 mL. This procedure was repeated twice more and the resulting concentrate (Lip-NO-Fe) was used for the reduction studies as monitored by ESR. UV-visible spectra of the colorless filtrate solutions indicated that little leakage of the $K_3Fe(CN)_6$ out of the liposomes had occurred during the concentration process. Nitroxide doped liposomes containing entrapped buffer (Lip-NO) were prepared in a similar manner. Liposomes were used within 12 h of the last concentration step.

ESR-Monitored Reduction Studies with Ascorbate

Figure 2:
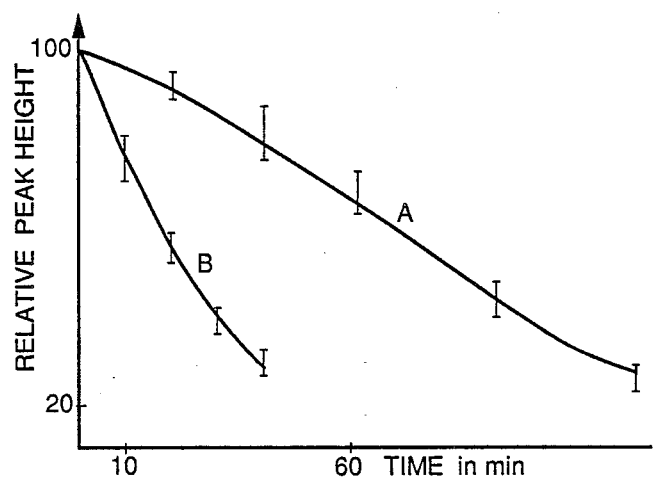
FIG. 2 is a graph of ESR signal intensity vs. time for a liposome of the type shown in FIG. 1.

A chilled 40-μl aliquot of Lip-NO-Fe (pH 8, see above) (50 μl in the case of Lip-NO) was placed in a melting point capillary. This was positioned inside a quartz ESR tube and allowed to equilibrate at 0° C. for 10 min. Then 4 μl (1 μl of 0.5 Molar sodium ascorbate in the case of Lip-NO) of freshly prepared sodium ascorbate dissolved in 1.0 mL of 0.05M TRIS HCl buffer, pH 8.0, 0.1M KCl) at 0° C. was added via a chilled syringe, with agitation provided by movement of the syringe needle. The rate of reduction of nitroxide (3) was monitored by measurement of the peak height of the low-field line of the nitroxide triplet as a function of time (FIG. 2). Similar results were obtained by monitoring the double integral of the peak versus time.

$A_{410}$ nm-Monitored Reduction Studies with Ascorbate

Figure 3:
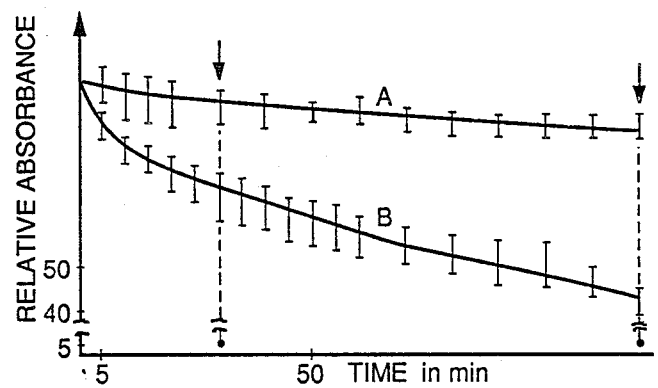
FIG. 3 is a graph of corrected absorbance at 410 nm vs. time.

A chilled solution (1.0 mL) of Lip-NO-Fe or Lip-Fe was placed in a quartz UV cuvette and allowed to equilibrate at 5° C. under a $N_2$ atmosphere (minimizes fogging of the cell and prevents air oxidation of the EYL) for 15 min. Then a 25 μl or 50 μl aliquot of 1.0M sodium ascorbate solution (see above) wa added via a chilled syringe. The rate of reduction of the entrapped $K_3Fe(CN)_6$ was monitored by the intensity change in its visible absorption maximum at 410 nm as a function of time (FIG. 3). A correction for small base line drifts was made by subtracting out changes in absorbance observed at 500 nm, a region of near transparency. Plotted on the ordinate is $$\frac{(A_{410} - A_{500})t = 0}{(A_{410} - A_{500})t = 0} \times 100$$

The lipid bilayer impermeant oxidant $K_3Fe(CN)_6$ was used in this experiment. Rozantsev, et al. [Synthesis (1971) 190–202] previously oxidized N-hydroxy compounds to nitroxides using aqueous $K_3Fe(CN)_6$, but at pH >13. It was thus first necessary to determine whether this oxidizing agent was capable of rapidly oxidizing the relatively persistent N-hydroxy secondary amine (1) to nitroxide (2) at pH 6–8. As mentioned above, mixing equimolar amounts of $K_3Fe(CN)_6$ and (1) did lead to rapid conumption of the $K_3Fe(CN)_6$ (20–25 percent remained after 10 min.), establishing the suitability of this oxidizing agent at suitably low pH values.

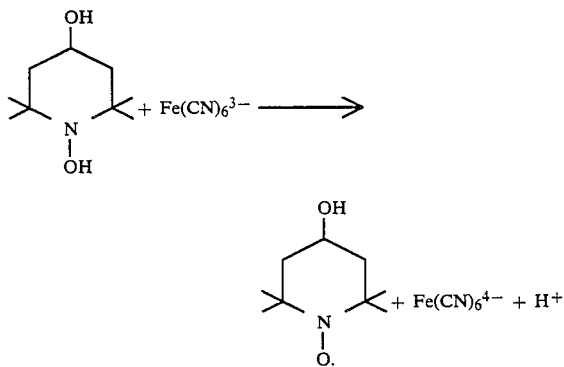

Unilamellar liposomes were prepared in buffered $K_3Fe(CN)_6$ solution using egg yolk lecithin both in the presence and absence of nitroxide fatty ester (3). The liposomes were purified by gel filtration and showed a visible absorption maximum at 410 nm (e, 1072; cf. e, 8 at 410 m for ester 3) characteristic of $K_3Fe(CN)_6$. Mason and Hwang [*Ann. N.Y. Acad. Sci.* 308) 29–49 (1978)] have estimated the number of phospholipid molecules per liposome (aggregation number) to be 2,678 and the internal aqueous volume of an average liposome to be $6.83 \times 10^{19}$ cm$^3$ for a comparable liposome preparation. Similar estimates have been reached by Tabushi et al. [*J. Am. Chem. Soc.* 106: 219–226 (1984)] for $K_3Fe(CN)_6$-containing liposomes. Using these data it is estimated that on the average each nitroxide-doped liposome entraps about 200 molecules of $K_3Fe(CN)_6$ and contains about 130 molecules of nitroxide 3 in the bilayer, or approximately a two-fold excess of oxidant over nitroxide.

Liposomes containing nitroxide (3) showed no ESR spectrum before gel filtration owing to the well known ESR spectral broadening effect of $K_3Fe(CN)_6$. After gel filtration an ESR spectrum was taken by the procedure described by Birrell et al., *J. Am. Chem. Soc.* 95: 2451–2458 (1973). The spectrum showed the desired characteristics of nitroxide x-axis anisotropic motion, i.e. rotation about the long axis of nitroxide (3) within the liposome. Only those nitroxide groups oriented toward the exterior of the liposome gave rise to the observed ESR signal since the inner nitroxide signal was expected to be broadened by the $K_3Fe(CN)_6$.

The behavior of the ESR signal from liposomes containing nitroxide (3) and internalized $K_3Fe(CN)_6$ in the presence of an excess of the external reductant, ascorbate ion, was observed. Ascorbate ion was chosen as the external nitroxide reductant owing to its extensive use as a mild, bilayer impermeant (at 5° C.), water soluble nitroxide reductant of physiological significance as mentioned by D. Hornig in *Ann. N.Y. Acad. Sci.* 258: 103–118 (1975). FIG. 2 shows a plot of the peak height of the low-field ESR line versus time, both in the presence and absence of internalized oxidant. Note that despite the 10-fold increase in the external concentration of ascorbate in the case of Lip-NO-Fe the ESR signal decay was much slower than in the case of Lip-NO. These experiments show that the nitroxide signal remains some 4–5 times longer when internal oxidant is present than not.

An indirect confirmation of the above results was obtained by monitoring the amount of $K_3Fe(CN)_6$ present in the liposomes by visible absorption spectroscopy at 410 mg. A plot of absorbance (corrected for small baseline shifts) at 410 nm versus time for several liposome-nitroxide-ascorbate combinations at 5° C. is shown in FIG. 3. Curve A shows that relatively little reduction of the internalized $K_3Fe(CN)_6$ occurred in the presence of excess external ascorbate when the liposomes did not contain nitroxide (3). Essentially the same initial absorbance was observed with liposomes that had been stored at 5° C. for several hours prior to the experiment. This latter observation demonstrates that the internalized ferricyanide does not leak out of the liposome to a significant extent over the time course of the reduction experiment and is consistent with the observation of others. Had leakage occurred, then lower initial absorbance values would have been observed after addition of excess ascorbate. Addition of n-propanol (see upside down arrow) to the system described in curve A causes an immediate and rapid reduction of the ferricyanide ions by the excess ascorbate. n-Propanol destroys the integrity of the liposome as described in Newman et al., *Biochemistry* 14: 3363–3370 (1975). This allows the two aqueous phases to come into contact with concomitant direct reduction of ferricyanide by ascorbate.

Curve B shows that a significant increase in the rate of reduction of internalized ferricyanide ion by external ascorbate occurs when nitroxide (3) is present in the phospholipid bilayer. Thus, a shuttling of electrons from ascorbate ion into the aqueous compartment mediated by the nitroxide group must be taking place, likely by the flip-flop mechanism discussed above.

Thus, a liposome-internalized oxidant can serve to regenerate a nitroxide group that has suffered reduction to the diamagnetic N-OH group at the external surface of the liposome. The internally regenerated nitroxide may then flip to the outside surface of the liposome where it once again is available to serve as a contrast enhancer for MRI.

II. Substances Incorporating Numerous Nitroxide Free Radicals

A second embodiment of the invention employs large molecules, particularly polymeric molecules, or assemblies of molecules, particularly liposomes, constructed to have numerous, i.e. at least about ten, persistent nitroxide free radicals. Because there are so many persistent nitroxide free radicals, the reduction of a few such free radicals is of little significance. Such large molecules or polymers are not merely carriers of encapsulated contrast agents. They are, themselves, the contrast agents since their surfaces are covered with persistent nitroxide free radicals.

A. Liposomes Constructed from Amphipathic Molecules Containing Nitroxide Free Radicals One such construction is a nitroxide-doped liposome formed by sonication of amphipathic molecules having persistent nitroxide groups. A suitable amphipathic molecule has a polar head group, at least two chains and a nitroxide group sufficiently near the head group that the nitroxide can contact bulk water when in a liposome. As a general rule, the nitroxide must be ten carbons or less from the head group for there to be effective bulk water contact. Particularly well suited are double chain amphipathic molecules having a nitroxide group near the polar end of each chain. To be effective as a sustained use contrast agent, substantially all the amphipathic molecules that make up the liposome should cntain at least one nitroxide group. Most advantageously, the polar head group will also have at least one nitroxide.

EXAMPLE 2

3-proxylpalmitic acid is synthesized by a procedure which parallels the proxyl nitroxide synthetic route described in U.S. Pat. No. 4,099,918, which is incorporated herein by reference. Nitrone (4) (commercially available from Aldrich Chemical Co.) was allowed to react with tridecylmagnesium bromide in ether to give an N-hydroxy intermediate which was immediately oxidized with $Cu^{2+}$ and $O_2$ to give nitrone (5).

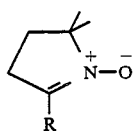

R = H    (4)

R = $CH_3(CH_2)_{12}$    (5)

Next, (5) was allowed to react with allylmagnesium bromide in ether and then the reaction was quenched by the addition of acetyl chloride to give N-acetoxy pyrrolidine (6). Selective oxidation of the terminal double bond of (6) to give carboxylic acid (7) was accomplished using the $RuO_4$-$CCl_4$-MeCN reagent combination described by Carlsen et al. in "A Greatly Improved Procedure for Ruthenium Tetroxide Catalyzed Oxidation of Organic Compounds", *J. Org. Chem.* 46: 3936–3938 (1981).

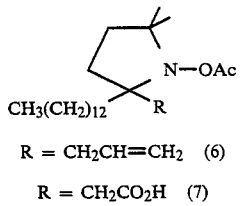

R = $CH_2CH=CH_2$    (6)

R = $CH_2CO_2H$    (7)

Hydrolysis of (7) with methanolic sodium hydroxide under air followed by acidification gave the nitroxide 3-proxylpalmitic acid (8).

The syntheses of the new amphipathic nitroxide-bearing molecules proceeded as follows. The carboxyl group of (8) was activated by formation of the mixed anhydride (9) using ethyl chloroformate and triethylamine.

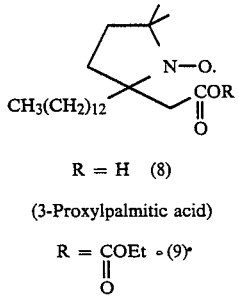

R = H    (8)

(3-Proxylpalmitic acid)

R = $\underset{\underset{O}{\|}}{C}$OEt    (9)

The anhydride (9) was then used to diacylate the two primary amino groups of N,N-bis(2-aminoethyl)methyl amine, by the procedure of Riggio et al., "50. Specific Ligands for the Affinity Chromatorgraphy of Cholinergic Proteins", *Helv. Chim. Acta* 63: 488–497 (1980), to give diamide (10).

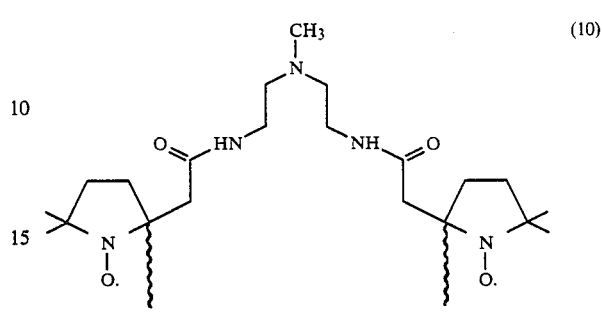

Diamide (10) contains a reactive tertiary amino group that was quaternized by alkylation to give a series of amphipathic molecules containing a nitroxide group near the polar end of each chain. Thus, alkylation of (10) with methyl iodide gave quaternary salt (11) while methyl bromide gave quaternary salt (12). Alkylation was also accomplished using a nitroxide-bearing alkyl group. The quaternary salt (13) was thus obtained by alkylation of (10) with 3-bromomethyl-2,2,5,5-tetramethylpyrroline-1-oxyl [Hankovszky et al., "Nitroxyls. VII. Synthesis and Reactions of Highly Reactive 1-oxyl-2,2,5,5-tetramethyl-2,4-dihydropyrrole-3-ylmethyl sulfonates", *Synthesis* 914–916 (1980)]. This unique amphipathic molecule contains three nitroxide groups, all of which are near the polar end of the molecule.

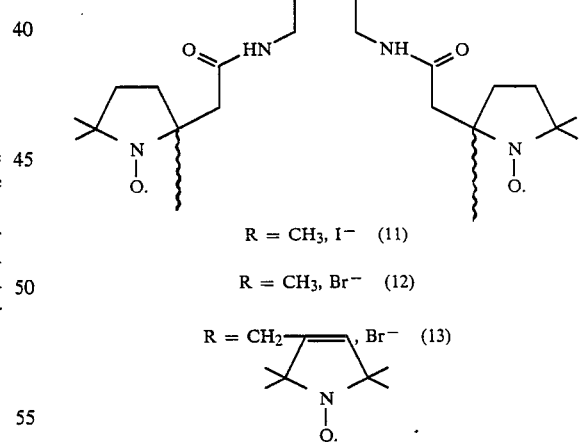

R = $CH_3$, $I^-$    (11)

R = $CH_3$, $Br^-$    (12)

R = $CH_2$—⟨⟩, $Br^-$    (13)

The quaternary salt (13) is a preferred species because of the third nitroxide associated with its polar head group. It should be understood, however, that R could be almost any group except for a large nonpolar group that would prevent the amphipathic molecule from forming a liposome. R can be an alkyl or aromatic group with or without hetero atoms and with or without nitroxides. However, one could also substitute an aryl-alkyl group, a heterocyclic group, another carbocyclic group or a group of the formula:

wherein X is a leaving group. R may have additional functional groups such as ester groups, ether groups and amino groups. If R has charged functional groups, such as carboxyls, phosphates or sulfates, it can include up to about fifteen carbons, otherwise it should include no more than about eight carbons.

The choice of an anion for the salt is similarly non-critical, but a biocompatible ion, such as chlorine, should be used. Other biocompatible anions include $HCO_3^-$, $PO_4^{3-}$, $HPO_4^{2-}$, $H_2PO_4^-$, $HSO_4^-$, $SO_4^{2-}$, $CH_3CO_2^-$, succinate, citrate and propionate.

The ability of such amphipathic molecules to form liposomes (vesicles) was demonstrated using electron microscopy (EM). EM allows the direct visualization of liposome formation using a new amphipathic molecule and is the usual method for doing so as described for example in Kunitake et al., *J. Am. Chem. Soc.* 99: 3860-3861 (1977); and Rupert et al., "Fusogenic Behavior of Didodecyldimethylammonium Bromide Bilayer Vesicles", *J. Am. Chem. Soc.* 107: 2628-2631 (1985). EM demonstrated that (11), (12) and (13) all form liposomes upon sonication of their respective aqueous solutions.

It is the outer surface of (11), (12) and (13)-derived liposomes that is in contact with the bulk water. The nitroxide groups on this outer surface should be in a position to efficiently contact the bulk water and effect magnetic relaxation. $T_1$ measurements at 360 mHz indeed confirmed the effectiveness of these liposomes. Whereas the $T_1$ value for pure water was 3.3. sec (control), a value of 0.7 sec was measured for a $5 \times 10^{-3}$M "solution" of (11) in water.

Preparation of Nitrone (5)

5,5-Dimethyl-1-pyrroline-N-oxide (4) (5.52 g, 0.040 mol) was added with stirring to the Grignard reagent prepared from Mg (1.21 g, 0.05 mol) and 1-bromotridecane (13.2 g, 0.50 mol) in ether (200 mL). After 1.5 h at 25° C. saturated aqueous ammonium chloride (20 mL) and water (20 mL) were added. The ether layer was separated and washed with brine and evaporated. The residue was taken up in MeOH (200 mL) containing concentrated ammonium hydroxide (10 mL) and Cu(OAc)$_2$·H$_2$O (1 g). Oxygen gas was bubbled through the solution until a deep blue color presisted. The solvent was evaporated and the residue was dissolved in CHCL$_3$. This was washed with saturated aqueous NaHCO$_3$ and then dried (MgSO$_4$). Evaporation of the solvent gave 11.3 g (95 percent) of nitrone (5) as a colorless oil (single spot by TLC, R$_f$ 0.45, 10:1 CHCl$_3$—MeOH) suitable for the next reaction. IR (form) 1589 cm$^{-1}$; NMR (CDCl$_3$) δ0.88 (t, 3), 1.25 (s, 20) 1.40 (s, 6), 1.51 (m, 2), 1.97 (t, 2), 2.47 (t, 2), 2.56 (t, 2).

Preparation of Acetate (6)

A 11.3-g (0.04 mol) sample of nitrone (5) was dried by addition and azeotropic removal of benzene. To the dry nitrone was added a 1.0M solution (60 mL, 0.06 mol) of allylmagnesium bromide in ether. After a 30 min stir at 25° C. the mixture was cooled to 0° C. and acetyl chloride (6 mL, 0.08 mol) was added dropwise. After 1 h at 25° C. the cloudy mixture was poured over ice and the ether layer was separated and washed with saturated aqueous NaHCO$_3$ and brine. The dried (MgSO$_4$) solution was concentrated to dryness, giving 13.2 g of an orange oil which was purified by flash chromatography over silica gel. Elution with 25:1 hexane-ethyl acetate gave 6.5 g (43 percent) of acetate (6) (single spot by TLC, R$_f$=0.23, 25:1 hexane-EtOAc) as a light yellow oil suitable for the next reaction and 1.8 g (13 percent) of the corresponding nitroxide as a byproduct. Spectra of (6): IR (film) 1775, 1639 CM$^{-1}$; NMR (CDCl$_3$) δ0.88 (t, 3), 1.15 (s, 6), 1.25 (s, 24), 1.64 (m, 4), 2.06 (s, 3), 2.25 (m, 2), 5.04 (m, 2), 5.90 (m, 1).

Preparation of Acid (7)

To a solution of (6) (1.70 g, 4.5 mmol) in CCl$_4$ (12 mL), MeCN (12 mL), and water (18 mL) were added NaIO$_4$ (5.26 g, 24.6 mmol) and RuCl$_3$·3H$_2$O (36 mg). The two phase mixture was stirred at 25° C. for 2 h and then the mixture was extracted with CH$_2$Cl$_2$. The extract was dried (MgSO$_4$) and evaporated, giving 1.3 g (73 percent) of acid (7) as a pale yellow oil suitable for the next reaction: one spot by silica gel TLC, R$_f$=0.65 (4:3, hexane-EtOAc); IR (film) 1771, 1748 cm$^{-1}$; NMR (CDCl$_3$) δ0.88 (t, 3), 1.19 (s, 6), 1.25 (s, 24), 1.65 (m, 4), 2.18 (s, 3), 2.31-2.52 (ABq+m, 2).

Preparation of 3-Proxylpalmitic Acid (8)

Acid (7) (1.20 g, 3.0 mmol) was dissolved in MeOH (50 mL) and then 2.5N NaOH (4 mL) was added. The solution was allowed to stand at 25° C. for 1 week and then most of the solvent was evaporated. Water (25 mL) was added and the mixture was extracted with ether. The ether extract was discarded and the aqueous phase was cooled to 0° C., acidified with 1N HCl, and extracted with ether. The ether extract was dried (MgSO$_4$) and evaporated to give nitroxide (8) (0.80 g, 75 percent) as a thick yellow oil suitable for the next reaction: one spot by silica gel TLC, R$_f$=0.22 (4:3 hexane-EtOAc); IR (film) 3400-2700, 1710 cm$^{-1}$; ESR (CHCl$_3$) 3 lines, $a_N$—15.6 G.

Preparation of Mixed Anhydride (9)

To a 0° C. solution of (8) (106.2 mg, 0.300 mmol) in ether (5 mL) was added triethylamine (41.3 μL, 0.300 mmol) and ethyl chloroformate (30.1 μL, 0.300 mmol). The reaction mixture was stirred for 2 h at 25° C. and then filtered. Evaporation of the filtrate gave mixed anhydride (9) (130 mg, 100 percent) suitable for the next reaction: IR (film) 1821, 1761 cm$^{-1}$.

Preparation of Bisamide (10)

To a solution of N,N-bis(2-aminoethyl)-methylamine (17 mg, 0.15 mmol, Aldrich Co.) in THF (0.5 mL) was added a solution of (9) (130 mg, 0.30 mmol) in THF (1 mL). After a 2 h stir at 25° C. the yellow solution was evaporated and the residue was flash chromatographed on silica gel. Elution with 80:30:5 CHCl$_3$-acetone-MeOH gave bisamide (10) (84 mg, 75 percent) as a thick yellow oil suitable for the next reaction: one spot by silica gel TLC, R$_f$=0.74 (75:25:3 CHCl$_3$—MeOH—water); IR (film) 3344, 1668, 1652 cm$^{-1}$; ESR (CHCl$_3$) 3 lines, $a_N$=15.0 G.

Preparation of Quaternary Ammonium Bromide Salts (11) and (12)

To a 0° C. solution of bisamide (10) (15.8 mg. 0.020 mmol) in acetone (2 mL) was added a 2M solution (0.2 mL, 0.4 mmol) of bromomethane in ether. The resulting solution was stirred at 25° C. for 24 h. The reaction was monitored over this time period by TLC over silica gel (75:25:3 CHCl₃—MeOH—water) and shown to be complete. The reaction mixture was evaporated to dryness, giving bromide salt (12) (17.7 mg, 100 percent) as a yellow oil (single spot by TLC, $R_f$=0.59, 75:25:3 CHCl₃—MeOH—water): IR (film) 3266, 1668 cm⁻¹; ESR (MeOH) 5 lines, $a_{N/2}$=8.25 G.

Preparation of Quaternary Ammonium Iodide Salt (11)

The preparation of 8 was analogous to that of (12) described above. From 15.8 mg of (10) and 56.8 mg of iodomethane there was obtained 18.6 mg (100 percent) of salt (11): one spot by silica gel TLC, $R_f$=0.59 (75:25:3 CHCl₃—MeOH—water); IR (film) 3285, 1665 cm⁻¹.

Preparation of Quaternary Ammonium Bromide Salt (13)

This salt was prepared by combining bisamide (10) with a 5-fold excess of 3-bromomethyl-2,2,5,5-tetramethyl-3-pyrroline-1-oxyl and heating the mixture at 45° C. solvent for five days. The excess alkylating agent was removed by high vacuum to give (13) as a thick orange oil: one spot by silica gel TLC, $R_f$=0.60 (75:25:3 CHCl₃—MeOH—water).

Preparation of Liposomes from Salts (11), (12) and (13)

Quaternary salts (11), (12) and (13) (10 mg) were separately dissolved in CHCl₃ and the solution was evaporated in vacuo such that it coated the wall of a flask. Then 10 mL of distilled water was added, resulting in an emulsion. The mixture was sonicated for 3 min at 40 W below 35° C. The slightly turbid mixture was centrifuged at 27,000×g for 3 min, resulting in a clear pale yellow solution. A few drops were mixed with one percent aqueous uranyl acetate and applied to a carbon grid and electron micrographs were recorded in the usual way.

T₁ Measurement on Vesicles Derived from (11)

Vesicles of (11) were prepared in distilled water as described above and then diluted with an equal volume of distilled water. The solution was deoxygenated by bubbling Ar through the solution was for 10 min. This solution used in the inversion-recover experiment (180°−τ−90°) for the T₁ measurements. The probe was detuned by 9 MHz to avoid the radiation feedback described by Hobson et al. in "Some Effects of Radiation Feedback in High Resolution NMR", [J. Magn. Resonance 20: 458–474 (1975). The null occurs between 0.5 and 1.5 sec. The integrals of the resonance peaks of water versus the corresponding time, τ, were used to fit the nonlinear function I=A(1−[1+W(1−exp (−k/T₁)] exp (−τ/T₁), which generates the plot A=amplitude at τ>T₁, k=time between pulse sequences, w=−(amplitude at τ=0)/A, I=peak intensity. This function corrects for the error introduced by the inability of the instrument to achieve a perfect 180° inverting pulse [Levy, I. Peat, "The Experimental Approach to Accurate Carbon-13 Spin Lattice Relaxation Measurements", J. Magn. Resonance 18: 500–521 (1975)]. For this experiment T₁ is calculated to be 0.7±0.1 sec. (control: $T_{1(water)}$=3.3 sec).

EXAMPLE 3

Another approach is to acylate lysophosphatidyl choline (palmitoyl) with 3-proxylstearic acid (14).

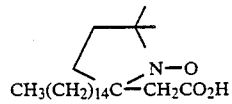

(14)

This will give a phosphatidyl choline (PC) with one nitroxide chain in which the nitroxide is near the polar headgroup.

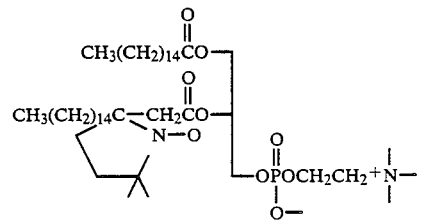

Next, the quaternary ammonium group is monodemethylated to a tertiary amine and then requaternized with a nitroxide-containing alkylating agent. This will give a PC with two nitroxide groups at the polar end (necessary to be sufficiently near the polar end so that water molecules can contact them and thus become relaxed in an MRI application).

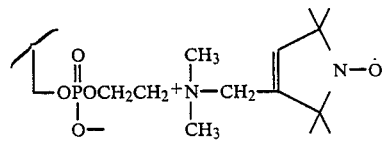

EXAMPLE 4

As another alternative glycerolphosphoryl choline

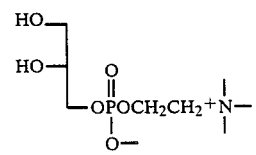

can be diacylated with the aim of introducing two nitroxide-bearing chains in the lipid portion of the PC molecule. Addition of another at the polar end will give three.

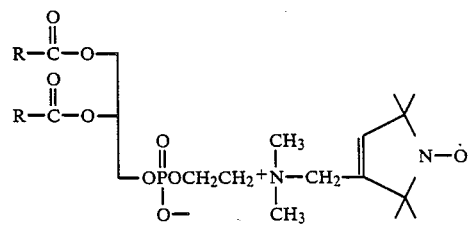

R = carbon chain containing a nitroxide group

EXAMPLE 5

Proxyl nitroxides can be used to prepare triple nitroxide analogs of non-phospholipid molecules known to form liposomes.

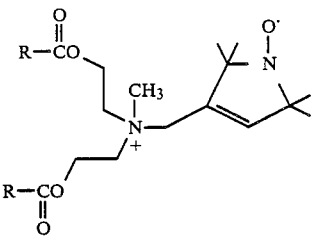

R = carbon chain containing a nitroxide group

B. Nitroxide-Doped Polymers

May polymeric molecules can be doped with nitroxides to provide contrast agents. Candidates include almost any linear or branched, amino or hydroxy functionalized polymer that is not highly toxic and that has a molecular weight not more than about 10,000. Examples include polylysine and polyvinyl alcohol.

To produce a contrast agent molecule covered with nitroxide groups, a polymer molecule can be populated with any nitroxide group that bears a charge. A polymer could, for example, be populated with acyl nitroxides, phosphoryl nitroxides and/or aromatic nitroxides. A polymer with multiple hydroxyl groups can be esterified with a carboxylic acid, carboxylic anhydride or acyl halide that has a bound nitroxide such as nitroxide of the type described in Keana, "Synthesis and Chemistry of Nitroxide Spin Labels," Chapter 1 in Holtzmann, J. L., ed., *Spin Labeling in Pharmacology*, Academic Press, New York (1984) and U.S. Pat. No. 4,099,918. The resulting ester has such a great number of nitroxide groups that a normal reduction of nitroxides does not significantly reduce MRI contrast, even when the ester is administered at a low concentration.

EXAMPLE 6

Arborols are cascade molecules of a type recently described by Newkome et al. in *J. Org. Chem.* 50: 2003 (1985) and in *J. Am. Chem. Soc.* 108: 849–50 (1986), both of which are incorporated herein by reference. The arborol molecules or polymers are characterized by a multiply-branched tree-like structure extending from a common core. The arborols preferably have an approximately spherical or circular hydrophylic surface covering a compact lipophilic core. An example is the benzene [9]$^3$-arborol (20):

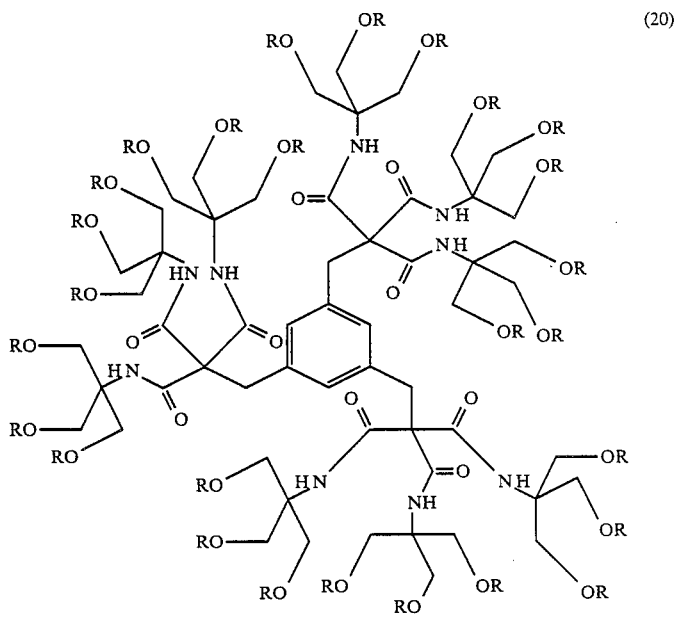

(20)

wherein R=H. The arborol (20) can be esterified to provide an ester with nitroxide groups. The ester can have R groups that, for example, are acyl nitroxides, phosphoryl nitroxides and/or aromatic nitroxides.

EXAMPLE 7

Another form of nitroxide-bearing polymer can be formed by utilizing the method of Newkome et al., *J. Org. Chem.* 50: 2004–2006 (1985), but beginning with 5,5-dimethoxypentanal (21) so that the single alkyl group terminates in a reactive group (an aldehyde after acidic hydrolysis)

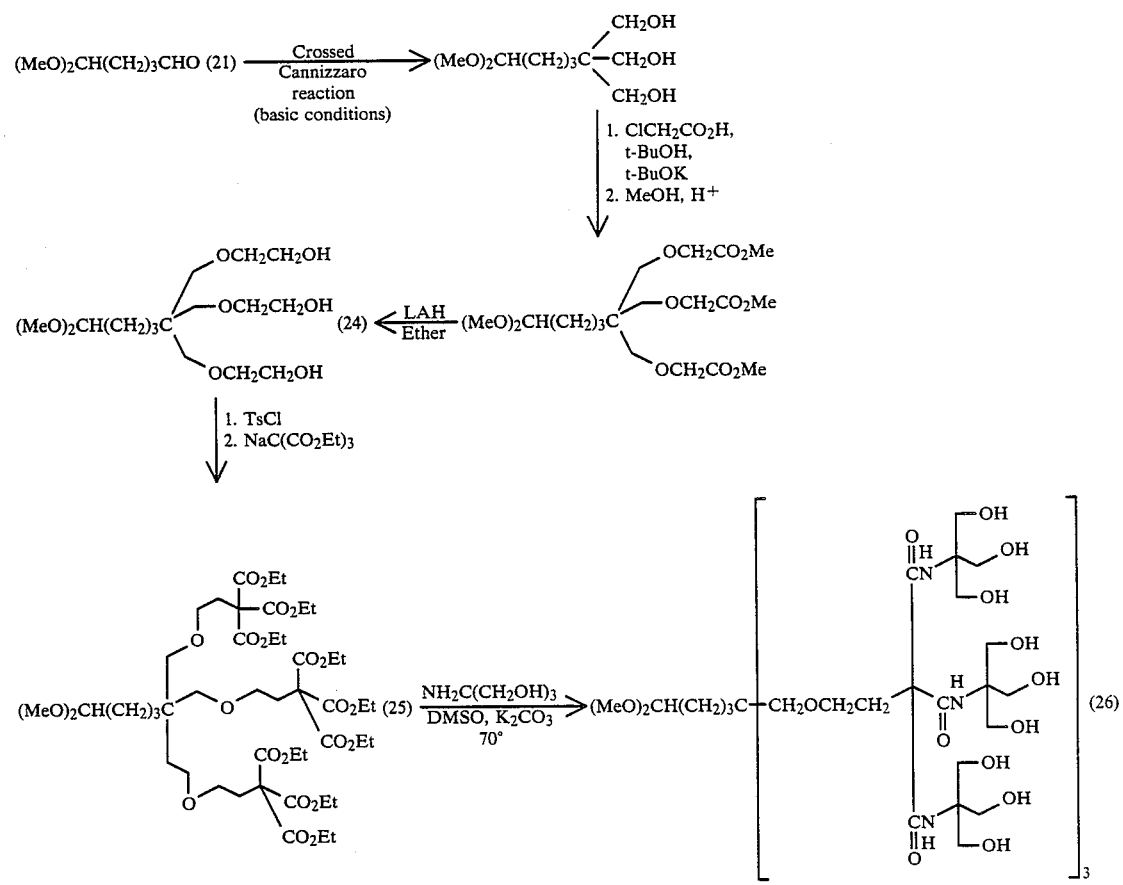

Twenty-seven nitroxidses are then attached to (26) by esterification with

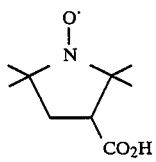

(27)

III. Tissue Specific Nitroxide Contrast Agents

There is a natural tendency for liposomes to target the liver and spleen, where they are rapidly taken up. For nitroxide compounds of the present invention to be more widely applicable, rapid take-up by the liver and spleen can be inhibited by synthesizing molecules that have either irreversibly or reversibly polymerizable long chains as described in Hupfer et al., "Liposomes from Polymerizable Phospholipids" *Chem. Phys. Lipids* 33: 355-374 (1983); and Samuel et al., "Polymerized-depolymerized vesicles. Reversible thiol-disulfide-based phosphatidylcholine membranes", *J. Am. Chem. Soc.* 107: 42-47 (1985), each of which articles is incorporated therein by reference. Polymer-encased liposomes can be formed by the method of Regen et al., "Polymer-Encased Vesicles", *J. Am. Chem. Soc.* 106: 2446-2447 (1984); and Fukuda et al., "Polymer-Encased Vesicles Derived from Dioctadecyldimethylammonium Methacrylate", *J. Am. Chem. Soc.* 108: 2321-2327 (1986), each of which articles is incorporated herein by reference.

To target tissues other than the liver and spleen, antibodies can be bound to the nitroxide-bearing liposomes and polymers described herein. Antimyosin has potential for MRI of infarcted heart muscle. Preparation of antifibrin has been reported by Hui et al. in "Monoclonal Antibodies to a Synthetic Fibrin-Like Peptide Bind to Human Fibrin but not Fibrinogen," *Science*, 222: 1129-1131 (1983). This antibody would be expected to concentrate at the sites of blood clots, where fibrin has been formed. A liposome or polymer attached to antifibrin could be injected upstream of the target to provide MRI contrast for imaging clots and thrombin in blood vessels.

One cannot simply add more and more simple single tail nitroxides to a liposome then attach an antibody. Eventually, after about 50 percent or so of the total lipid tails is a single tail, as one would have by increasing the percentage of nitroxide fatty ester in, say, a phospholipid liposome, then the liposome becomes unstable and no longer suitable for targeting by an antibody or other device.

To provide effective targeted nitroxide molecules and assemblies of molecules, one can employ the liposomes or polymers described herein to build antibodies tagged with hundreds of nitroxides.

Attachment of antibodies to liposomes is accomplished, for example, by spiking a liposome with phosphatidyl ethanolamine or any other long tailed amine that will remain in the bilayer. The antibody is then conjugated to the amine. Specific procedures for the attachment of antibodies to liposomes are discussed in Martin et al., "Immunospecific Targeting of Liposomes to Cells," *Biochemistry*, 20: 4229–4238 (1981), and in Huang et al., "Coupling of Antibodies with Liposomes", Chapter 4, *Liposome Technology: Volume III. Targeted Drug Delivery and Biological Interaction*, G. Gregoriadis, Ed., CRC Press, Boca Raton, Fla. (1984), both of which are incorporated herein by reference.

For polymers, a handle is provided for the attachment of an antibody. In the case of arborols, the handle can be one of the dendritic branches or can extend from the core of the molecule. The actual attachment would be accomplished by a technique like those used for the attachment of antibodies to liposomes.

There are other surface modifications which provide for cell recognition that could alter the biodistribution of liposomes and arborols. For example, carbohydrate receptor analogues bound to a liposome surface have been known to target the liposome. [Mauk et al., "Targeting of Lipid Vesicles: Specificity of Carbodyhydrate Receptor Analogues for Leukocytes in Mice," *Proc. Nat'l. Acad. Sci., U.S.A.* 77: 4430–4434 (1980); Mauk et al., "Vesicle Targeting: Timed Release for Leukocytes in Mice by Subcutaneous Injection," *Science*, 207: 309–311 (1980).] Such targeting by surface modifications are directly applicable for altering the biodistribution of nitroxide-bearing liposomes and polymers according to the present invention.

EXAMPLE 8

Yet another approach is to provide an arborol nitroxide-derivatized liposome. In this approach, a nitroxide labelled polymer is connected to a liposome by a long chain.

For example, an arborol poly alcohol is prepared as described by Newkome et al. in *J. Org. Chem.* 50: 2003 (1985) and in *J. Am. Chem. Soc.* 108: 849-50 (1986), except that the starting tribromide contains two long chains for anchoring it securely into the liposome bilayer. The several alcohol groups are esterified with nitroxide acids that bear additional polar groups. These groups then protrude into the bulk water and effect relaxation of the bulk water while the targeting is achieved through the attachment of the targeting agent to the parent liposome as described above. The synthesis proceeds as follows:

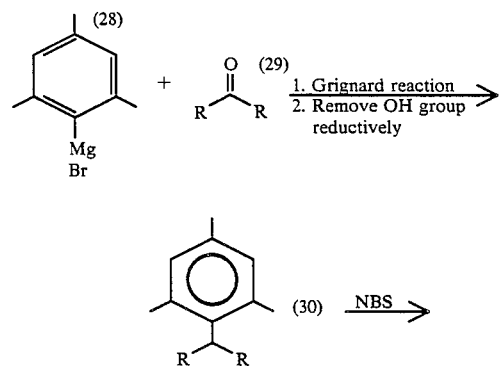

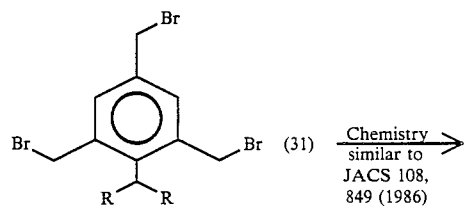

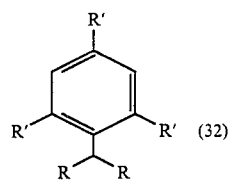

wherein, for example, R' is

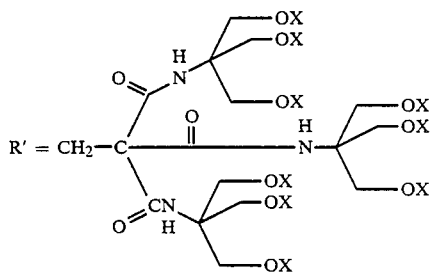

and x is,

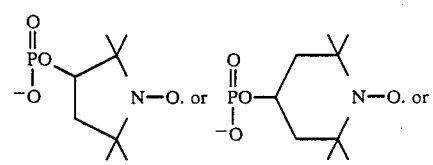

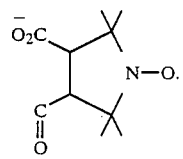

EXAMPLE 9

Another method of linking a liposome to a nitroxide-bearing polymer employs the pentaldehyde-centered polymer of Example 7 which results from esterification of (26) with (27). The acetal group of the polymer is cleaved with aqueous acid. Then, the polymer is reductively coupled, using NaBH$_3$CN, to liposomes containing phosphetidylethanolamine to provide

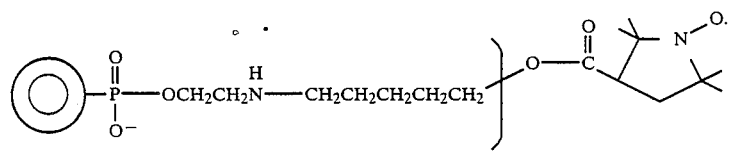

Targeting is provided by the liposome (represented above by concentric circles) while each coupled polymer provides twenty-seven nitroxides for MRI image enhancement.

Having illustrated and described the principles of my invention with reference to preferred embodiments, it should be apparent to those persons skilled in the art that such invention may be modified in arrangement and detail without departing from such principles. For example, liposomes can be prepared from nitroxide-containing amphipathic molecules containing more than two long chains, as described by Kunitake et al., "Bilayer Membranes of Triple-Chain, Fluorocarbon Ampiphiles", *J. Am. Chem. Soc.* 107: 692-696 (1985). I claim as my invention all such modifications as come within the true spirit and scope of the following claims.

I claim:

1. In an MRI contrast agent which is a liposome having a bound spin label that is subject to reduction, and thus loss of contrast enhancement capability when in a reducing environment, the improvement wherein the liposome incorporates oxidizing means for oxidizing and thereby restoring spin labels that have been reduced.

2. The contrast agent of claim 1 wherein the oxidizing means comprises an amount of an oxidant substance encapsulated within a compartment defined by the liposome.

3. A contrast agent of claim 1 in which an antibody, carbohydrate, or other cell recognition targeting agent is attached to the liposome to provide specific targeting.

4. An MRI contrast agent, the agent comprising:
   a liposome having a bilayer shaped to define a compartment;
   multiple nitroxides incorporated into the bilayer; and
   an oxidant substance inside the compartment.

5. The contrast agent of claim 4 wherein the oxidant substance comprises $K_3Fe(CN)_6$.

6. A contrast agent of claim 4 in which an antibody, carbohydrate, or other cell recognition targeting agent is attached to the liposome to provide specific targeting.

7. A diagnostic preparation comprising the MRI contrast agent of claim 4 in a biocompatible carrier liquid.

8. A method for enhancing the magnetic resonance image of a target tissue, the method comprising providing, in the target tissue, an MRI contrast agent according to claim 4.

9. An MRI contrast agent comprising a molecule or assembly of molecules, the molecule or assembly having at least ten nitroxide groups positioned to contact surrounding bulk water and effect magnetic relaxation.

10. A contrast agent of claim 9 in which an antibody, carbohydrate, or other cell recognition targeting agent is attached to the molecule to provide specific targeting.

11. The contrast agent of claim 9 comprising a nitroxide doped liposome.

12. The contrast agent of claim 11 comprising a liposome formed from amphipathic molecules, substantially all such molecules having at least one nitroxide group.

13. The contrast agent of claim 11 comprising a liposome formed from amphipathic molecules having at least two nitroxide groups.

14. The contrast agent of claim 11 comprising a liposome formed from amphipathic molecules having three nitroxide groups.

15. The contrast agent of claim 11 wherein the liposome is made up of amphipathic molecules of which the long chains are polymerizable such that, after polymerization of the chains, rapid take-up of the liposome by the liver and spleen is inhibited.

16. The contrast agent of claim 9 comprising a liposome formed from multiple chain amphipathic molecules attached to a polar group, each chain having a nitroxide group sufficiently near the polar group that the nitroxide can contact bulk water.

17. The contrast agent of claim 16 wherein at least one of the amphipathic molecules have more than two chains.

18. The contrast agent of claim 16 wherein the polar group has at least one nitroxide group.

19. The contrast agent of claim 16 comprising a liposome formed from cations of the formula:

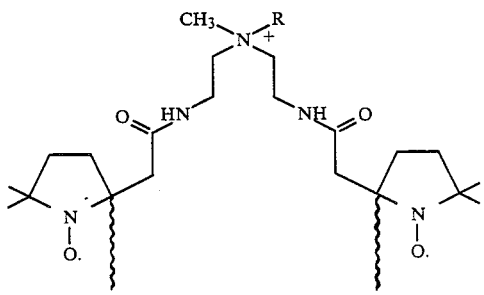

wherein R is an alkyl or aromatic group with or without hetero atoms present and with or without a nitroxide.

20. The contrast agent of claim 19 wherin R is —$CH_3$ or

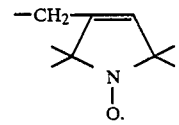

21. The contrast agent of claim 9 comprising a nitroxide-doped, linear or branched polymer of a molecular weight not more than about 10,000.

22. The contrast agent of claim 21 comprising an arborol of the formula:

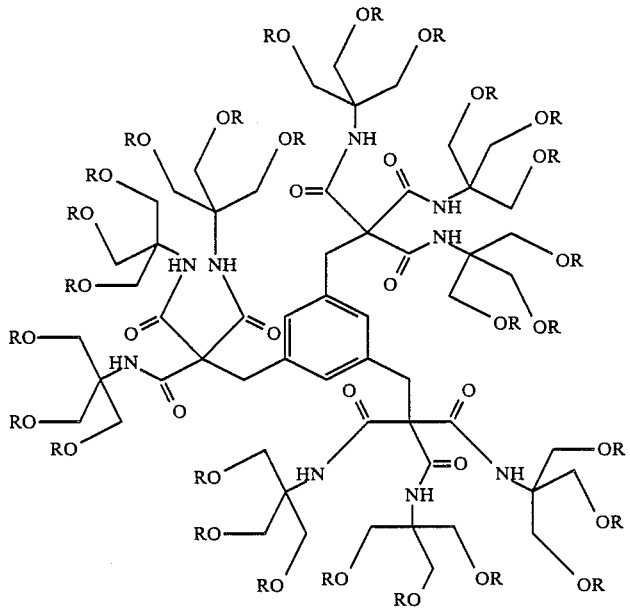

wherein R is an acyl nitroxide, phosphoryl nitroxide or aromatic nitroxide.

23. A diagnostic preparation comprising the MRI contrast agent of claim 9 in a biocompatible carrier liquid.

24. A method for enhancing the magnetic resonance image of a target tissue, the method comprising providing, in a target tissue, an MRI contrast agent comprising a molecule or assembly of molecules, the molecule or assembly having at least ten nitroxide groups positioned to contact surrounding bulk water and effect magnetic relaxtion, the agent being provided in an amount sufficient to enhance the magnetic resonance image of the target tissue.

25. The method of claim 24 in which an antibody, carbohydrate, or other cell recognition targeting agent is attached to the molecule to provide specific targeting.

26. The method of claim 24 wherein the contrast agent comprises a nitroxide doped liposome.

27. The method of claim 26 wherein the contrast agent comprises a liposome formed from amphipathic molecules, substantially all of such molecules having at least one nitroxide group.

28. The method of claim 26 wherein the contrast agent comprises a liposome formed from amphipathic molecules having at least two nitroxide groups.

29. The method of claim 26 wherein the contrast agent comprises a liposome formed from amphipathic molecules having three nitroxide groups.

30. The method of claim 26 wherein the contrast agent comprises a liposome made up of amphipathic molecules of which the long chains are polymerizable such that, after polymerization of the chains, rapid takeup of the liposome by the liver and spleen is inhibited.

31. The method of claim 26 wherein the contrast agent comprises a liposome formed from multiple double chain amphipathic molecules attached to a polar group, each chain having a nitroxide group sufficiently near the polar group that the nitroxide can contact bulk water.

32. The method of claim 31 wherein at least some of the amphipathic molecules have more than two chains.

33. The method of claim 31 wherein the polar group has at least one nitroxide group.

34. The method of claim 31 wherein the contrast agent comprises a liposome formed from cations of the formula:

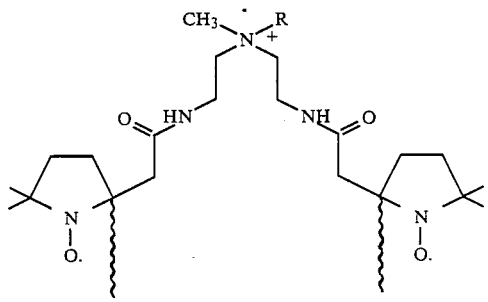

wherein R is an alkyl or aromatic group with or without hetero atoms present and with or without a nitroxide.

35. The method of claim 34 wherein R is —CH₃ or

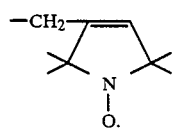

36. The method of claim 24 wherein the contrast agent comprises a nitroxide-doped, linear or branched polymer of a molecular weight not more than about 10,000.

37. The method of claim 36 wherein the contrast agent comprises an arborol of the formula

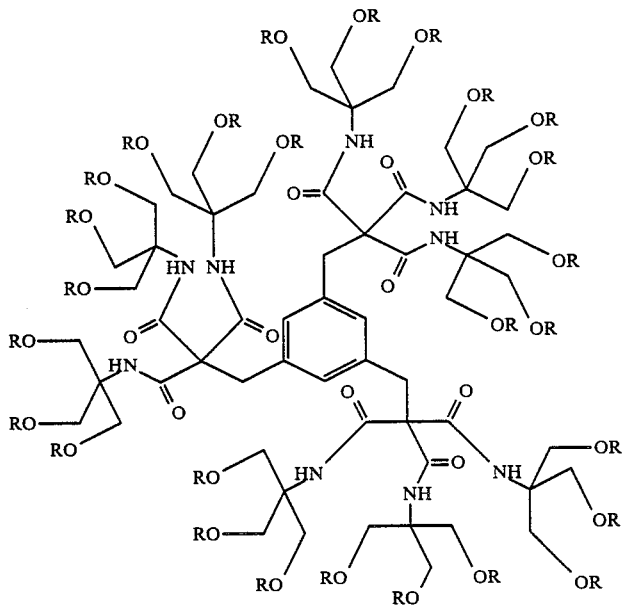

wherein R is an acyl nitroxide, phosphoryl nitroxide or aromatic nitroxide.

38. The method of claim 36 wherein the arborol is bound to a liposome.

39. The method of claim 38 in which an antibody, carbohydrate, or other cell recognition targeting agent is attached to the liposome to provide specific targeting.

40. A salt of the cation:

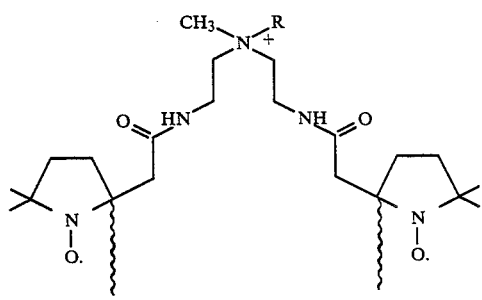

wherein R is an alkyl or aromatic group with or without hetero atoms present and with or without a nitroxide.

41. The salt of claim 40 wherein R is —CH$_3$ or

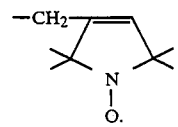

42. A salt of claim 40 wherein the anion is a halide.
43. A liposome formed from a salt of claim 40.
44. An arborol of the formula:

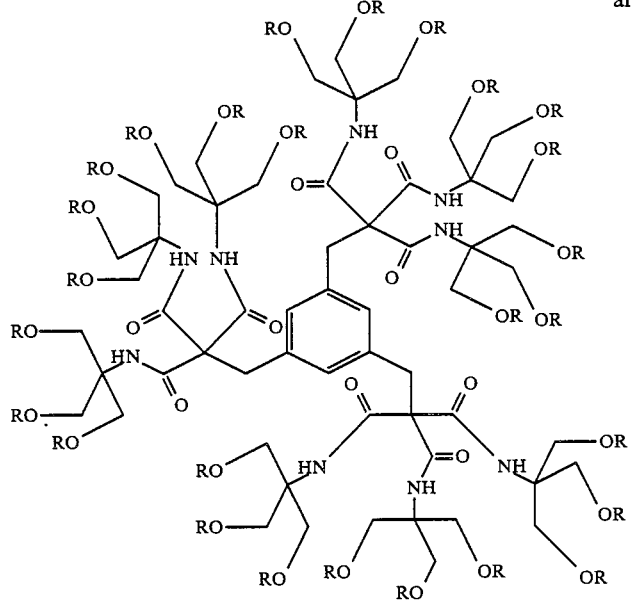
wherein R is an acyl nitroxide, phosphoryl nitroxide or aromatic nitroxide.
* * * * *